(12) United States Patent
Dahmen

(10) Patent No.: US 9,297,954 B2
(45) Date of Patent: Mar. 29, 2016

(54) LIGHT CONDUCTOR WITH A BUNDLE OF OPTIC FIBERS AND A METHOD FOR BENDING THE LIGHT CONDUCTOR

(71) Applicant: Karl Storz GmbH & Co. KG, Tuttlingen (DE)

(72) Inventor: Jan Dahmen, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 320 days.

(21) Appl. No.: 13/745,364

(22) Filed: Jan. 18, 2013

(65) Prior Publication Data
US 2013/0223802 A1   Aug. 29, 2013

(30) Foreign Application Priority Data

Jan. 20, 2012   (DE) .......................... 10 2012 200 794

(51) Int. Cl.
| | |
|---|---|
| *G02B 6/06* | (2006.01) |
| *G02B 6/04* | (2006.01) |
| *A61B 1/07* | (2006.01) |
| *G02B 23/24* | (2006.01) |
| *A61B 1/00* | (2006.01) |
| *F21V 8/00* | (2006.01) |
| *A61B 1/005* | (2006.01) |

(52) U.S. Cl.
CPC ................ *G02B 6/04* (2013.01); *A61B 1/0011* (2013.01); *A61B 1/00167* (2013.01); *A61B 1/07* (2013.01); *G02B 6/0008* (2013.01); *G02B 23/2469* (2013.01); *A61B 1/005* (2013.01); *Y10T 156/1002* (2015.01)

(58) Field of Classification Search
None
See application file for complete search history.

(56) References Cited

U.S. PATENT DOCUMENTS

| | | | | |
|---|---|---|---|---|
| 4,076,377 | A * | 2/1978 | Moraschetti | 385/116 |
| 4,718,417 | A * | 1/1988 | Kittrell et al. | 606/7 |
| 5,335,647 | A * | 8/1994 | Brustad | 600/139 |
| 5,465,315 | A | 11/1995 | Sakai et al. | |
| 5,554,100 | A * | 9/1996 | Leiner et al. | 600/182 |
| 6,101,703 | A * | 8/2000 | Odanaka | 29/447 |
| 7,308,177 | B1 | 12/2007 | Raszka et al. | |
| 2002/0120181 | A1 | 8/2002 | Irion | |
| 2006/0036132 | A1 | 2/2006 | Renner et al. | |
| 2007/0088201 | A1 | 4/2007 | Eisenkolb | |

FOREIGN PATENT DOCUMENTS

| | | |
|---|---|---|
| DE | 6903790 U | 5/1969 |
| DE | 69325477 T2 | 3/2000 |
| DE | 10200195 A1 | 7/2003 |
| DE | 102005051208 A1 | 4/2007 |
| DE | 202008001786 U1 | 12/2008 |
| JP | 03081717 A * | 4/1991 |

* cited by examiner

*Primary Examiner* — Hemang Sanghavi
(74) *Attorney, Agent, or Firm* — Whitmyer IP Group LLC

(57) ABSTRACT

A light conductor having a bundle of optic fibers to transmit light, and a method for bending the light conductor made up of optic fibers. The light conductor with a bundle of optic fibers to transmit light of a light source, which can be coupled onto a first end portion of the light conductor, to a second end portion of the light conductor, includes a first portion and a curved second portion configured as a connecting portion, where the optic fibers in the second portion are fixed in place with respect to one another, free of tension, by means of a hardened cementing agent, while maintaining the curvature.

15 Claims, 8 Drawing Sheets

A-A

B-B

C-C

D-D

E-E

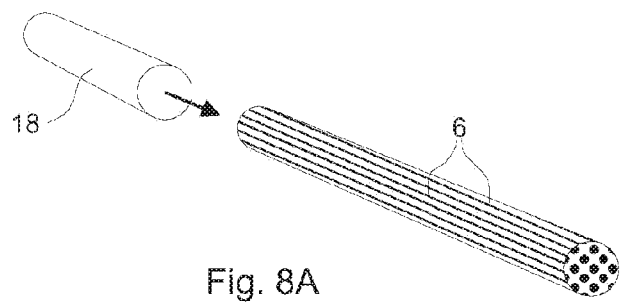
Fig. 8A
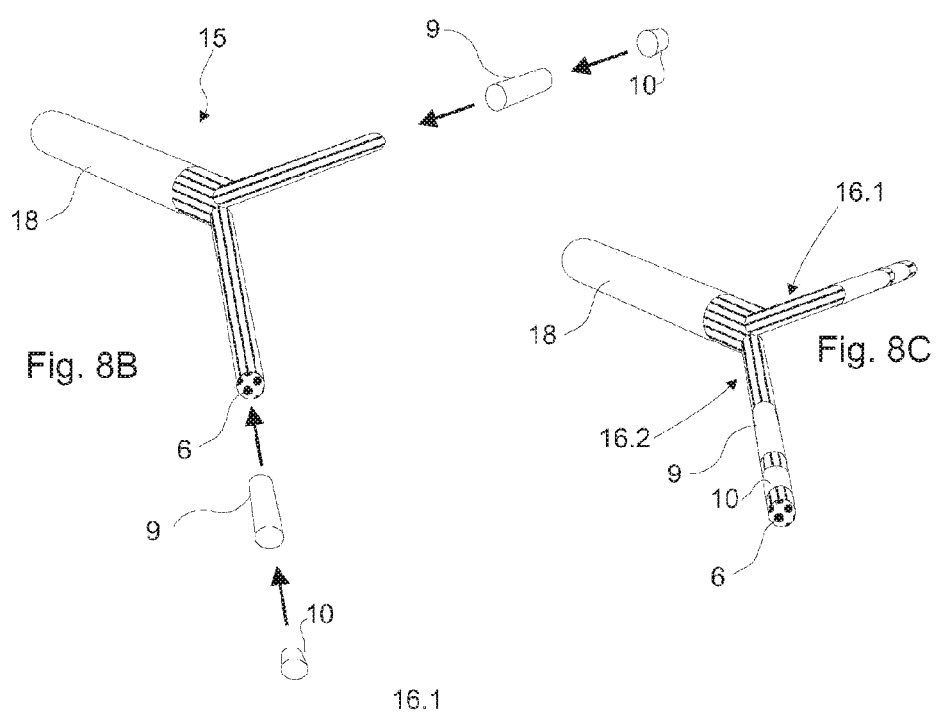
Fig. 8B
Fig. 8C
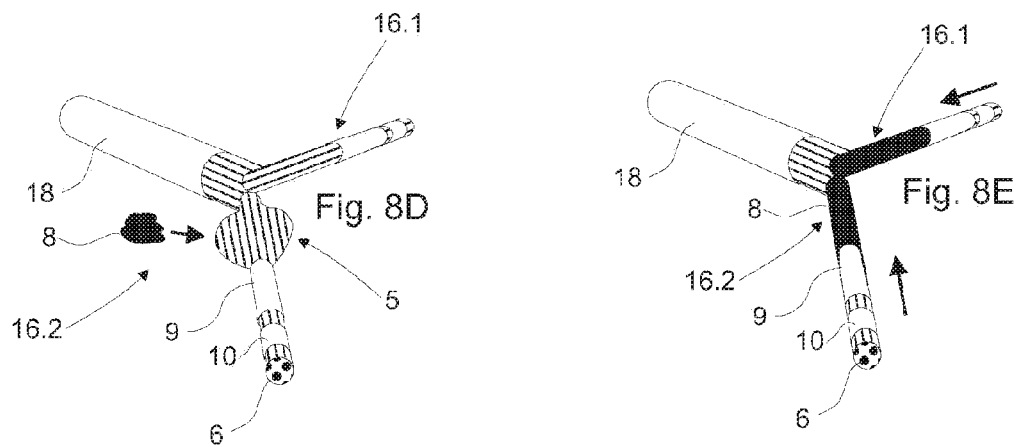
Fig. 8D
Fig. 8E

LIGHT CONDUCTOR WITH A BUNDLE OF OPTIC FIBERS AND A METHOD FOR BENDING THE LIGHT CONDUCTOR

FIELD OF THE INVENTION

The present invention relates to a light conductor having a bundle of optic fibers to transmit light, and to a method for bending the light conductor formed by the optic fibers.

BACKGROUND OF THE INVENTION

Light conductors made of optic fibers for transmitting light can be used to transmit signals or light.

Patent DE 202008001786 describes an elevator installation in which optic fibers are used in the pull cables for positioning the elevator cabin or monitoring a carrier belt.

It can occur that the fiber bundles must be bent for a period of time, so that the light conductor can also transmit the light or signal to the desired location.

Prior art in general teaches methods for bending fiber bundles to conduct light. For example, according to the state of the art, the bending or reshaping of the fiber bundle is performed with the help of a curling wedge. After the bending process, the curling wedge usually remains in the bent fiber bundle and is cemented to it. There is the risk, however, that the curling wedge is not held firmly enough by the solidified cement and can come loose from the bonding of the cementing agent and fiberglass. This can be particularly disadvantageous when the optic fibers are used in a medical device. In the worst case, the released wedge can be discharged inside the patient.

If the curling wedge is removed from the bent fiber bundle after the bending procedure, it leaves a gap, which must be filled with cement. The additional application of cement into the gap can result in a poor bond between the cement and the fiber bundle. This can lead to variable adhesion levels in the fiber bundle, particularly when the cement migrates to locations in the fiber bundle that restrict the lengthwise extension of the fiber bundle from fluctuations in pressure and temperature and reduce the mechanical strength, as can occur for example in sterilization by autoclave. As a result of insufficient capacity for lengthwise extension, individual fibers in the fiber bundle can be broken.

According to an additional method for bending fiber bundles of light conductors, the bending or reshaping of the fiber bundle is performed by making use of the geometric structure of the section of the apparatus housing that is provided to encase the fiber bundle. The fibers in this case are bent with the help of corresponding guidance and reception sections in the apparatus housing. This demands a housing with complex structure, which can be challenging and expensive in terms of planning and manufacture. With this method, the optic fiber bundles are usually fastened in the housing structure by means of a cement, although here as well it is not possible to ensure whether the cement remains in the position foreseen for it or if it migrates disadvantageously to other locations by capillary action of the fiber bundle. This, again, can lead to unintended fastening at some locations in the fiber bundle, which can cause disadvantageous pulling, pressing and crosswise tensions in the fiber bundle, especially in autoclaving.

SUMMARY OF THE INVENTION

Thus it is the object of the present invention to provide a light conductor and/or a method with which the aforementioned disadvantages can be resolved.

Said object is achieved with the features of the independent claims. Additional embodiments are indicated in the subsidiary claims, which are derived from the former.

One idea of the invention is to provide a fiber optic bundle with a bundle of optic fibers that comprises a first and a second portion, such that the second portion comprises a predetermined bending that is maintained by means of a cementing agent, such that the individual light-conducting fibers are fastened to one another essentially without tension. This effect is produced, first, by the application of a paste-like cementing agent to the fiber bundle and, then, by bending the portion bearing the paste-like cement into the required bent shape. The not-yet-hardened cementing agent allows the individual light-conducting fibers to slide toward one another upon bending so that no forced tensions are formed in the fiber bundle.

The inventive light conductor comprises a bundle of optic fibers to transmit light from a light source, which can be coupled to a first end portion of the light conductor, to a second end portion of the light conductor, such that said light conductor comprises a first portion and a curved second portion that is configured as a fastening portion, such that, according to the invention, the optic fibers in the second portion are fixed in place with respect to one another, essentially free of tension, by means of a hardened cement while maintaining the curvature. That is, the fibers are held stable in the area of the connecting portion, which is largely or completely free of tension and can be built into a housing in simple manner. No holding or supporting apparatuses are required in the housing for the connecting portion, which is stable in its own right. The advantage is that the bending does not produce forced tensions in the curved second portion, so that there is a marked reduction in the number of fibers that could otherwise break during bending. An additional advantage is that the inventive light conductor can be inspected easily, before it is built in, to find any broken fibers that are incapable of conducting any additional light. It is also possible for the connecting portion to be kept straight rather than curved. With the help of a corresponding bend radius r, the curvature can be indicated in the respective plane determined by the X-Y-Z coordinate system, such that bend radius can have a constant or varying curvature. To give a clearer sense of the term "curvature," reference is made to the following examples of geometric elements with varying curvature: The curvature of a straight line is equal to zero everywhere, because its direction does not change. A circle with a radius r has an equal curvature everywhere (that is, 1/r), because its direction changes everywhere to the same degree. In curves, the curvature and accordingly the bend radius change from curve point to curve point. "Curvature" in this context is therefore to be understood as a change in direction per continuing length of a sufficiently short portion of a curve of the particular optic fiber or fiber bundle.

In the inventive light conductor, the cementing agent is applied in the second portion of the optic fibers in such a way that the cement partly or completely surrounds the outer peripheral surfaces of the optic fibers and connects them with one another, so that the cement constitutes a self-supporting support frame, in which single or several or all optic fibers are embedded, in order to constitute the connecting portion so that no additional support apparatuses, especially in a housing, are required for the connecting portion. The advantage here is that the optic fibers are protected by the support frame made of hardened cement and held stable in the required bent position without requiring any additional supporting devices in a housing into which the light conductor can be built. In this way a simpler and more easily producible housing can be used for the inventive light conductor.

In an additional inventive embodiment of the light conductor, a flexible hose is applied on the second portion to stabilize it. Said flexible hose can be a cladding, which exerts a stabilizing effect on the optic fibers situated on the outer periphery of the light conductor and simultaneously also provides protection so that the cementing agent applied in the connecting portion is protected from substances that would otherwise attack the cementing agent. In particular, the cladding ought to be autoclaving-resistant and should be able to produce a corresponding protection for the cement situated in the connecting portion. The flexible hose has primarily the function of stabilizing the bundle of optic fibers against hardening of the cementing agent and of preserving the essentially circular shape of the optic bundle and in particular of supporting the optic fibers situated on the outer peripheral surface of the bundle, so that they remain in the connecting portion. This has the advantage that the outer optic fibers cannot be released from the connecting portion and in particular cannot break. An additional advantage of the cladding is that impacts acting on the connecting portion are not distributed onto individual fibers but rather onto the entire bundle. The flexible hose can be any cladding appropriate for stabilizing the circular shape of the optic bundle before the cement has hardened. In a preferred embodiment, the flexible hose is a shrink hose. In addition the cladding has the function of facilitating operation of the connecting portion that is provided with as yet unhardened cement, in particular to prevent soiling of the bending apparatus with glue in the bending process.

In an additional preferred embodiment of the inventive light conductor, on the first or second end portion of the light conductor a frame is mounted for insertion into an opening of an apparatus or housing of an apparatus for mechanical affixing of the light conductor. Said frame is preferably a frame that can be pushed into place and whose outer diameter corresponds with the inner diameter of an opening, for example in an illumination rod, endoscope or exoscope. It is also essential here that the frame is configured in such a way that the frame is suited for use in the inventive method for bending the light conductor, in particular in a bending apparatus used for the inventive method.

In an additional embodiment of the inventive light conductor, the frame is configured in the shape of a sleeve and the ends of the optic fibers on the outlet side of the frame have altogether a convex and/or concave and/or a flat surface, which preferably is polished or made smooth. This has the advantage that, with the frame, no single fibers can be broken off uncontrollably from the connecting portion during polishing, in particular in the peripheral area, possibly resulting in undesired diffusion of light. In addition, with the frame a plug-in connection is configured at the end of the light conductor, which facilitates easier insertion of the ends in corresponding recesses of apparatuses in which the inventive light conductor is used.

In another embodiment of the inventive light conductor, the frame is made of metal, a synthetic or a combination of metal and synthetic material. The frame is preferably a sleeve. In addition, the metal, synthetic or combination of metal and synthetic should be suited and biocompatible for medical use. PEEK plastic, in particular, can be used as the synthetic. What's essential in the materials used for the inventive light conductor is that they can be medically sterilized in an autoclave and that they should be biocompatible if necessary. Biocompatible materials are materials that have no negative impact and the highest possible tolerance with respect to patients. The shrink hose has in particular the function of facilitating operation of the connecting portion that is provided with unhardened cement and of preventing any soiling of the bending apparatus with cement in the process of curving the connecting portion.

According to an additional preferred embodiment of the inventive light conductor, the shrunken hose of the connecting portion is contiguous with the frame. This has the particular advantage that no gap can develop between the frame and shrunken hose and thus also no substances that attack the cementing agent can penetrate at this spot. The term "contiguous with" is understood as also meaning both the terms "neighboring on" and "bordering on." In addition the shrink hose can also extend into the frame and can be more or less overlapped by it. It is also conceivable that the shrink hose borders directly on the outer border of the frame or is set off at a short distance from it. In addition, the shrink hose has the function of facilitating operation of the connecting portion equipped with as yet unhardened cementing material, in particular to prevent a bending apparatus from being soiled with cementing material in the course of the bending process.

In an additional embodiment of the inventive light conductor, the first and second portions are configured in such a way that the optic fibers in the first portion have a first surface cross-section and in the second portion constitute a first, second and/or additional associated bundle into which the optic fibers of the first portion extend as a Y-shaped branch and each has a surface cross-section that is smaller than the first surface cross-section. It is conceivable that the optic fibers are divided into surface cross-sections of different size, for example to constitute a trident-shaped connecting portion. It is part of the inventive concept that the surface cross-section of the main strand can be divided into several single strands, which are then configured as a connecting portion. It is also part of the invention that the main strand remains unbranched and has a corresponding curvature in the connecting portion with a bend radius with constant or varying curvature.

According to another inventive embodiment of the light conductor, the optic fibers are configured of glass and/or synthetic fibers. Preferably, glass fibers with a glass core are used, said core having a diameter of approximately 70 micrometers and a glass coating of about 2.5 micrometers. The thickness of the glass fiber core can be in the range of 20 to 500 micrometers, such that the glass coating can be in the range of 3 to 5 micrometers. Optic fibers made of glass have the advantage of a very high light transmission along with very high light yield and at the same time can be autoclaved. It is also conceivable that the glass fiber core can be enclosed in a synthetic coating. The plastic or glass fiber coating preferably has a refractive index close to the refractive index of light. If the glass fibers are positioned in the inventive light conductor in such a way that each individual fiber is surrounded with air in its outer peripheral surface, it is possible to dispense with the glass or plastic coating.

The inventive light conductor is preferably used in an illumination apparatus. The illumination apparatus is used in medical procedures and/or apparatuses. As examples of an illumination apparatus, mention can be made, among others, of a head lamp, an endoscope that can be used inside a patient, an exospore (that is, an endoscope-type apparatus that can be used outside a patient), an illumination shaft or illumination rod with a rotator head. The inventive light conductor can in principle be used in any illumination apparatus. The preferred field of application for the inventive light conductor, however, is in medical apparatuses. The inventive light conductor, in particular, is configured in such a way that it can be repeatedly sterilized for medical purposes, in particular in autoclaves for medical sterilization.

According to an inventive method, the inventive light conductor is manufactured with a first portion and a curved second portion configured as a connecting portion of optic fibers, in such a way that the optic fibers of the second portion are moistened with a cementing agent that is in a non-hardened, paste-like condition. After application of the paste-like cement, the second portion is curved into a predetermined bent shape, such that the cement is still in a paste-like form. Only after this is the cement hardened while maintaining the bent shape of the second portion, until the second portion constitutes the dimensionally stable connecting portion made of optic fibers and hardened cement with predetermined bent shape. Applying cement in a paste-like non-hardened condition has the advantage that the fibers can be curved and upon curvature or bending can be slid toward one another, thus avoiding unnecessary stresses that can cause breakage of the fibers. Applying the cement with a paste-like viscosity to the second portion to configure the connecting portion has the advantage that the cement in this condition is less fluid and no migration of the cement from the point of application can occur.

The paste-like condition of the cementing agent refers to the viscosity of said cementing agent when applied or spread on, when the cementing agent has such a viscosity that, first, the cement or cementing agent can be spread and rubbed into the fiber bundle, so that essentially every fiber of the fiber bundle can be moistened with the cementing agent, without fibers breaking during spreading/massaging of the cement, and on the other hand the cement or cementing agent has such a low fluidity that the cementing agent or cement cannot migrate in the fiber bundle by capillary action.

According to another step in the inventive method for producing the inventive light conductor, before applying cement a shrink hose is pulled over a portion of the optic fibers situated close to the second portion and only after moistening the optic fibers with the cement is the shrink hose pulled over the portion coated with cement. This has the advantage that the portion coated with cement or cementing agent is protected by the shrink hose and, in particular during a bending process, does not seep laterally out of the optic fibers so as to soil the bending apparatus. In addition, the shrink hose has the task of stabilizing the fibers situated outside and relieving tensions to avoid breakage of fibers.

Further advantageous configurations of the invention, as well as embodiments of it, are described more closely hereinafter in connection with the appended drawings. Components having similar function are sometimes labeled with the same reference numbers. Terms such as "left," "right," "above" or "below" within the description of an embodiment refer to the drawings in an orientation with normally legible drawing depictions and reference numbers. To enhance clarity, the particular features in the following drawings are depicted schematically, in heightened manner and not to scale.

BRIEF DESCRIPTION OF THE DRAWINGS

The drawings are as follows:

FIGS. 8A through 8I show steps in the method for producing an inventive light conductor according to FIG. 3.

DETAILED DESCRIPTION OF THE EMBODIMENTS

Figure 1:
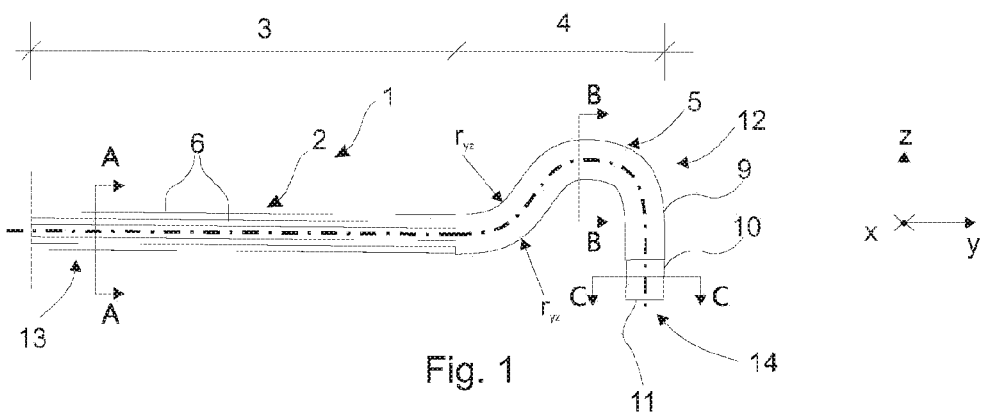
FIG. 1 shows a side view of an embodiment of the inventive light conductor.
Figure 2:
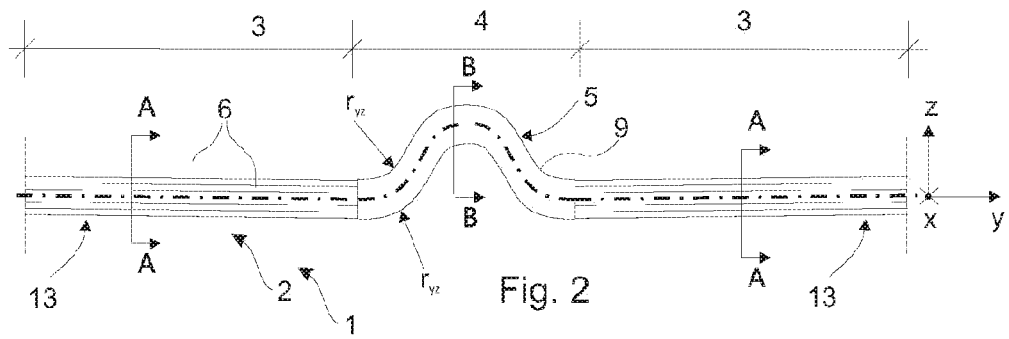
FIG. 2 shows a side view of an additional embodiment of the inventive light conductor.

FIGS. 1 and 2 show different embodiments of an inventive light conductor 1 with a first, flexible portion 3 and a second, curved portion 4. The light conductor 1 comprises a bundle 2 of optic fibers 6 for transmitting light from a light source, which can be coupled onto a first end portion 13 of the light conductor 1, to a second end portion 12 of the light conductor 1. The light source (not shown) is preferably a light source that can emit cold light, such as for example a xenon lamp, a halogen lamp or an LED. The bundle 2 of optic fibers comprises at least two optic fibers 6.

The inventive light conductor 1 shown in FIG. 1 comprises on its first end portion 13 the first flexible portion 3 and on its second end portion 12 the curved second portion 4, through both of which a bundle 2 of optic fibers 6 extend. In the flexible first portion 3, the optic fibers 6 can preferably slide with respect to one another in their longitudinal direction, that is, essentially in the Y direction. In the first portion 3 the movement of the single optic fibers is also not restricted in the X direction and the Z direction. The movement of the optic fibers 6 in the X direction and Z direction, however, can be restricted or prevented by a cladding.

Figure 1A:
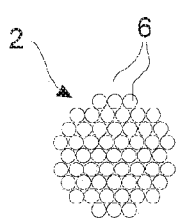
FIGS. 1A, 1B and 1C show sectional views of the light conductor seen in FIGS. 1 and 2 according to the section lines in FIGS. 1 and 2, in enlarged depiction.

In FIG. 1a, a cross-section view is shown according to the section line A-A from FIG. 1, such that to improve clarity the distances and diameters of the individual optic fibers 6 are not shown to scale but rather are enlarged.

The curved second portion 4 of the light conductor 1 is configured as a connecting portion or bending portion 5, which, by means of a hardened cementing agent 8, fixes the optic fibers in place with respect to one another, essentially free of tension, while maintaining a curvature with constant or variable bend radius r. The connecting portion or bending portion 5 comprises a hardened cementing agent 8, which preferably surrounds the individual optic fibers 6 of the inventive light conductor 1 in such a way that the cementing agent 8 acts as a support frame, such that the curved optic fibers 6 are situated as free of tension as possible in the support frame of the cementing agent 8. The hardened cementing agent 8 constitutes a support frame in which the individual optic fibers 6 are embedded. The essentially tension-free embedding of the optic fibers 6 is achieved through the fact that the cementing agent 8 with a paste-like viscosity is applied to the still non-curved second portion 4 and the second portion 4 with the still paste-like cementing agent 8 is curved into the required shape and the cementing agent 8 is hardened only after curving. The paste-like condition of the cementing agent refers to the viscosity of the cementing agent during coating or spreading, a process in which the cementing agent has such a viscosity that on the one hand the cement or cementing agent can be spread and massaged into the fiber bundle so that essentially every fiber of the fiber bundle can be moistened with cementing agent without fibers breaking during spreading/massaging of the cement, and on the other hand the cement or cementing agent has such a low fluidity that the cement or cementing agent cannot migrate in the fiber bundle by capillary action. Because the cementing agent is paste-like before bending the connecting portion 5 that is to be bent, the individual optic fibers 6 can slide with respect to one another in the paste-like cementing agent 8 during the bending process or curvature process without forced tensions developing on the individual optic fibers because of the bending process.

The preferred cementing agents 8 for use are cements that are paste-like before hardening and allow sliding of the individual optic fibers during the bending process, but that after hardening constitute a support frame that holds the individual optic fibers 6, as free of tension as possible, in their bend. In addition, the cementing agent 8 preferably has autoclave resistance, so that repeated sterilization of the connecting portion 5 is possible without the hardened cementing agent 8 being softened or dissolved by the sterilization process.

The cementing agent 8 in the preferred embodiment is a two-component cement, which is mixed in appropriate manner before application in and before the bending of the second portion 4, until the two components are mixed together to the required homogeneity and have the desired paste-like viscosity for application to the second portion 4.

Figure 1B:
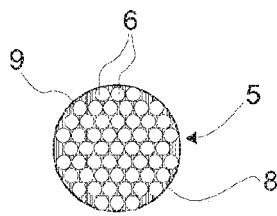

FIG. 1B shows a cross-section view according to the section line B-B from FIG. 1 through the connecting portion 5 in the second curved portion 4 of the inventive light conductor 1. As can be seen from FIGS. 1 and 1B, the connecting portion 5 is provided with a cladding 9 made of a flexible, closely adhering hose, for example a shrink hose, to stabilize the outer optic fibers 6. The cladding 9 is made of a material that has sufficient flexibility so that the connecting portion together with the non-hardened cementing agent 8 can be bent into the required shape, and in addition has a corresponding enclosing function or stabilizing function, so that the second portion 4 surrounded by the cladding 9 is held in an essentially circular shape, in particular in the bending process of the second portion 4. In the illustrated embodiment the cladding 9 is made of a transparent shrink hose of polyethylene terephthalate (PET) with a very thin wall thickness.

In FIG. 1 the curved second portion 4 or the connecting portion 5 is shown in the YZ plane with a bend radius $r_{yz}$. The connecting portion 5 can have a bend radius $r_{yz}$, with constant or varying curvature, depending on the required course of the connecting or bend portion 5, only in the YZ plane. The connecting portion 5 can also be configured as essentially straight and without curvature. However, depending on the use of the inventive light conductor, can be necessary that the connecting portion 5, also in the other planes of the coordinate system indicated in FIG. 1, is provided with a corresponding bend radius $r_{xy}$ and/or $r_{xz}$ with constant or varying curvature.

Figure 3:
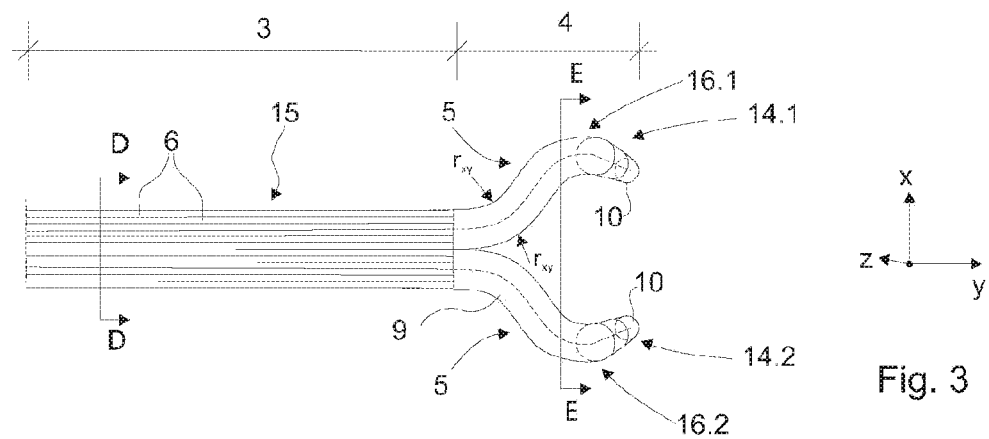
FIG. 3 shows an overhead view of another embodiment of the inventive light conductor.
Figure 3A:
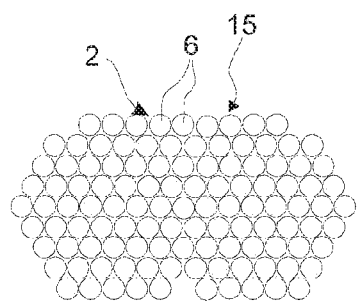
FIGS. 3A and 3B shows sectional views of the light conductor shown in FIG. 3 according to the section lines in FIG. 3.
Figure 3B:
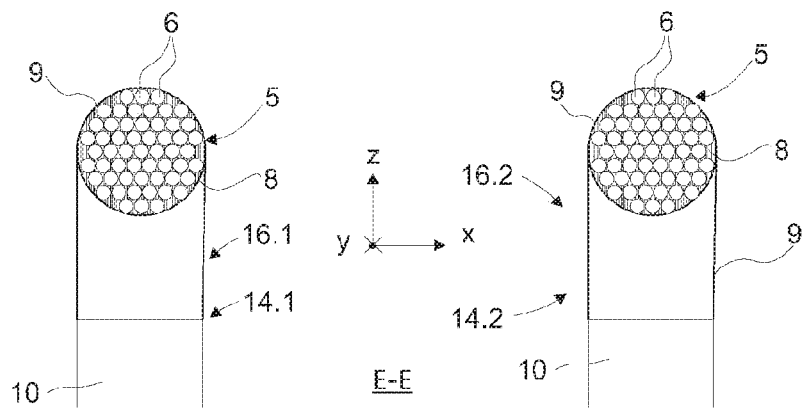

At the distal, light-emitting end portion 14 of the inventive light conductor 1, a frame or sleeve 10 is provided. FIG. 3C shows a cross-section view according to the section line C-C from FIG. 3 through the light-emitting end portion 14 of the inventive light conductor 1. The sleeve 10 is primarily provided at the light-emitting end portion 14 in order to make possible re-processing of the ends 11 of the optic fibers 6 of the light-emitting end portion 14, such as leveling or polishing, so that the polishing can prevent fraying of the bundle at the spot that is to be processed. As a result of polishing or grinding, the outlet surface configured by the ends 11 of the optic fibers 6 can be re-processed into a level, convex or concave surface. The sleeve or frame 10 in the illustrated embodiment is made of metal, in particular a biocompatible and autoclavable metal, that is suited for use in medical procedures. The sleeve can be produced from a biocompatible synthetic such as polyether ether ketone (PEEK).

The optic fibers 6 provided in the second, curved portion 4 can be provided with the same cementing agent in the entire connecting portion 5. It is also conceivable, however, that different cementing agents with varying firmness after hardening are applied in the second, curved portion. If two different cementing agents that have varying firmness in the hardened condition are used for the connecting portion 5, then preferably the cementing agent 8 used in the light-emitting end portion 14 in the area of the sleeve 10 is less elastic in the hardened condition than the hardened cementing agent 8 in the curved portion 4 between the sleeve 10 and the flexible portion 3. In other words, the hardened cement 8, in the curved portion 4 between the sleeve 10 and the flexible portion 3, comprises a smaller E module than the hardened cement in the light-emitting end portion 14 encased by the sleeve 10. The hardened cement 8, in the curved portion 4 between the sleeve 10 and the flexible portion 3, is then similarly elastic as latex or rubber, such that the hardened cement 8 in the light-emitting portion 14 enclosed by the sleeve 10 is inelastic and brittle instead, so that polishing and smoothing of the optic fibers 6 is possible at the outlet surface 11 on the light-emitting portion 14.

Figure 1C:
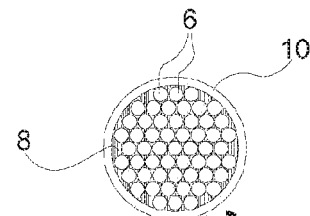

As can be seen from the sectional views in FIGS. 1B and 1C, the optic fibers 6 should individually be surrounded by the cementing agent 8 so that each individual optic fiber 6 is firmly fixed by the hardened cementing agent 8, free of tension, in the connecting portion 5 and in the light-emitting end portion 14.

FIG. 2 shows an additional inventive embodiment of the inventive light conductor 1, such that the connecting portion 5 with shrink hose 9 is not provided at a light-emitting end portion of the glass fiber bundle, but instead at an intermediate portion of a first, flexible portion 3.

The optic fibers 6 in the bundle 2 of the inventive light conductor 1 shown in the drawings are preferably glass fibers 6, in particular glass fibers 6 having a glass core 600 with a diameter of about 20 to 500 micrometers, which is surrounded by a glass coating 601 with a somewhat constant thickness of approximately 2.5 micrometers.

Figure 1D:
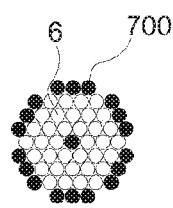
FIG. 1D shows a sectional view of an embodiment of the bundle of optic fibers of the inventive light conductor in enlarged depiction.
Figure 1E:
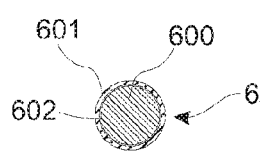
FIG. 1E shows a cross-section view of an optic fiber, in particular of a glass fiber, for use in the inventive light conductor, in a considerably enlarged depiction.

FIG. 1E shows a cross-section of an optic glass fiber 6, which is used in the inventive light conductors. The glass fiber 6 comprises a glass core 600, which is surrounded by a glass coating 601. The glass core 600 is configured from a glass suitable for light transmission, such that the glass coating 602 is made of a glass or synthetic that has a refractive index that corresponds approximately to the refractive index of air. The coating material 602 surrounding the glass core 600 should, in addition, meet the following conditions. The material used for the coating 601 may not be mixed with the glass core 600 during production of the optic fibers 6, so that there should exist a clear separating layer 602 between the coating 601 and the glass core 600. In addition, in the separating layer 602 between the glass core 600 and the coating 601, no vacant spaces should be present, because vacant spaces can have a negative impact on light transmission. Moreover, the glass or synthetic that is to be used must be biocompatible and autoclavable.

It is also possible that single or several optic fibers 6 can be produced completely, that is, both core and coating, of a light-conducting synthetic material, especially the optic fibers 6 that are subjected to an especially large bend or curvature in the bundle 2, such as for instance the optic fibers close to the center point of the approximately circular-shaped bundle 2 made of optic fibers 6. In FIG. 1D the optic fibers configured of synthetic material are indicated by way of example with the number 700 and filled in with black. As can be seen from this, in particular the optic fibers 700 on the outer peripheral surface and at the center point are configured of a light-conducting synthetic material. In principle, the fibers 6 that are exposed to an especially strong curvature can be produced from a suitable, elastic synthetic material, while the less curved fibers 6 can be made of glass.

Figure 4:
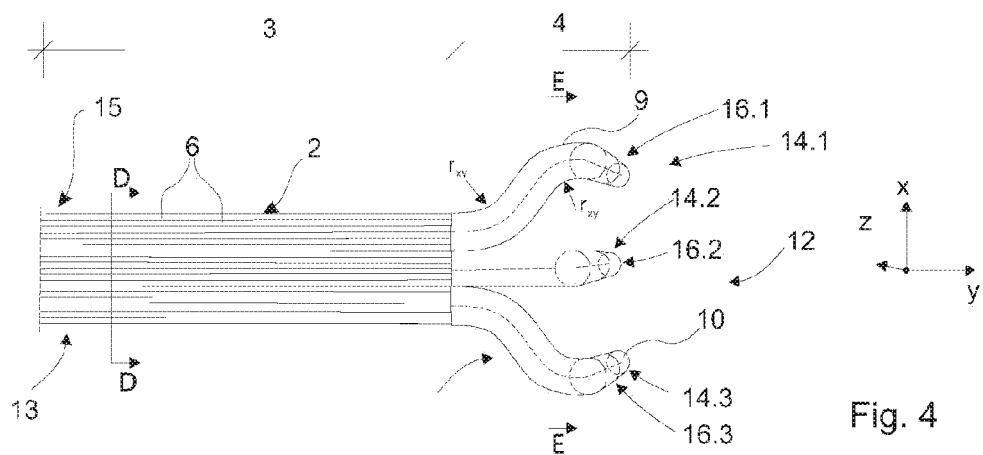
FIG. 4 shows an overhead view of an additional embodiment of the inventive light conductor.
Figure 4A:
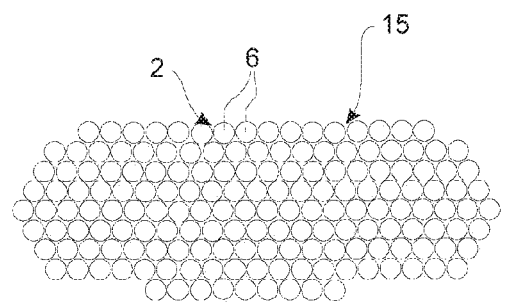
FIGS. 4A and 4B show sectional views of the light conductor shown in FIG. 4 according to the section lines in FIG. 4.
Figure 4B:
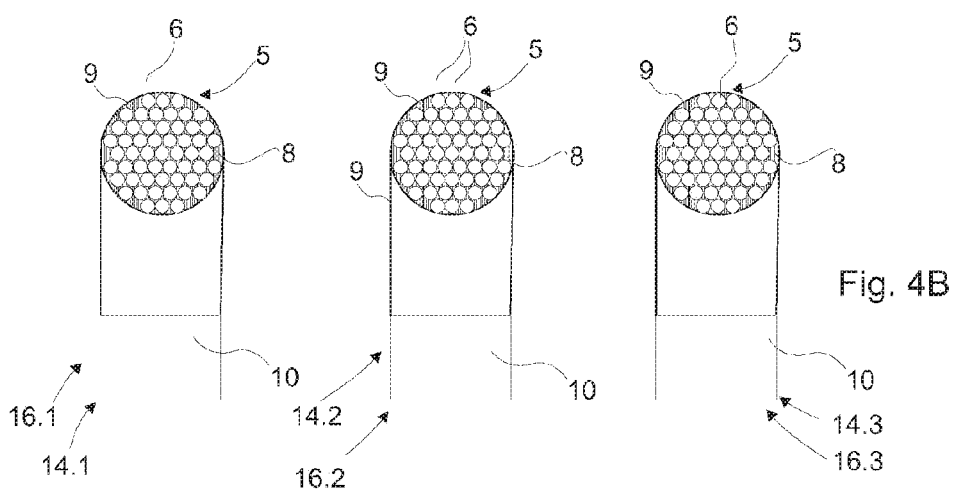

Shown in FIGS. 3 and 4 are additional embodiments of the inventive light conductor 1, in particular of the configuration of the bend portion or connecting portion 5.

The connecting portion 5 can be configured as a single-strand portion with an essentially constant surface cross-section as shown in FIG. 1 and the sectional views from FIGS. 1A through 1C, or else as a multi-strand portion as shown in FIGS. 3 and 4.

Illustrated in FIGS. 3 and 4 are embodiments of the division of the main strand 15 of the bundle 2 made of optic fibers 1 into various subsidiary strands 16.1, 16.2, 16.3. The overhead view shown in FIGS. 3 and 4 corresponds to a view of the XY plane according to the three-dimensional coordinate system shown in FIG. 3.

FIG. 3 shows the inventive light conductor 1 with a main strand 15 having a predetermined surface cross-section A, which extends in a Y shape into two subsidiary strands 16.1 and 16.2 each having a predetermined surface cross-section B1 and B2 into a first subsidiary strand 16.1 and into a second subsidiary strand 16.2. The surface cross-sections B1 and B2 are preferably essentially identical. It is also possible, however, to provide the surface cross-sections B1 and B2 each with different surface cross-sections. The subsidiary strands are each curved in the connecting portion 5 in the XY plane with a bend radius $r_{xy}$ as indicated in FIG. 3 and in the other planes with bend radii $r_{xz}$ and $r_{yz}$. The light-emitting end portions 14.1 and 14.2 are curved in the YZ plane corresponding to the curve radius $r_{yz}$ indicated in FIG. 1.

Figure 6:
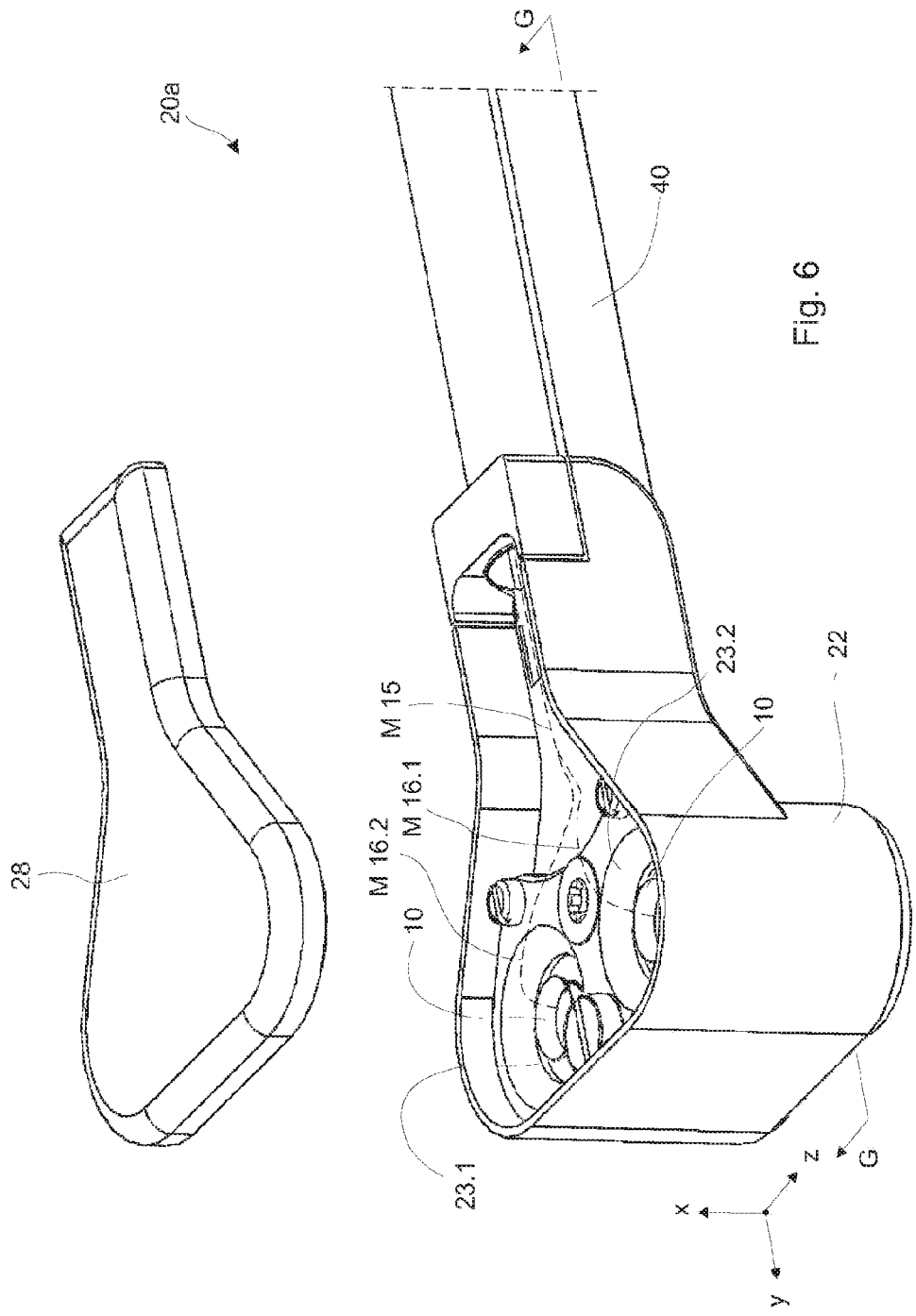
FIG. 6 shows a perspective view of an illumination shaft for the inventive light conductor from FIG. 3, such that, of the inventive light conductor, only the sleeves and respective center axes are shown.
Figure 7:
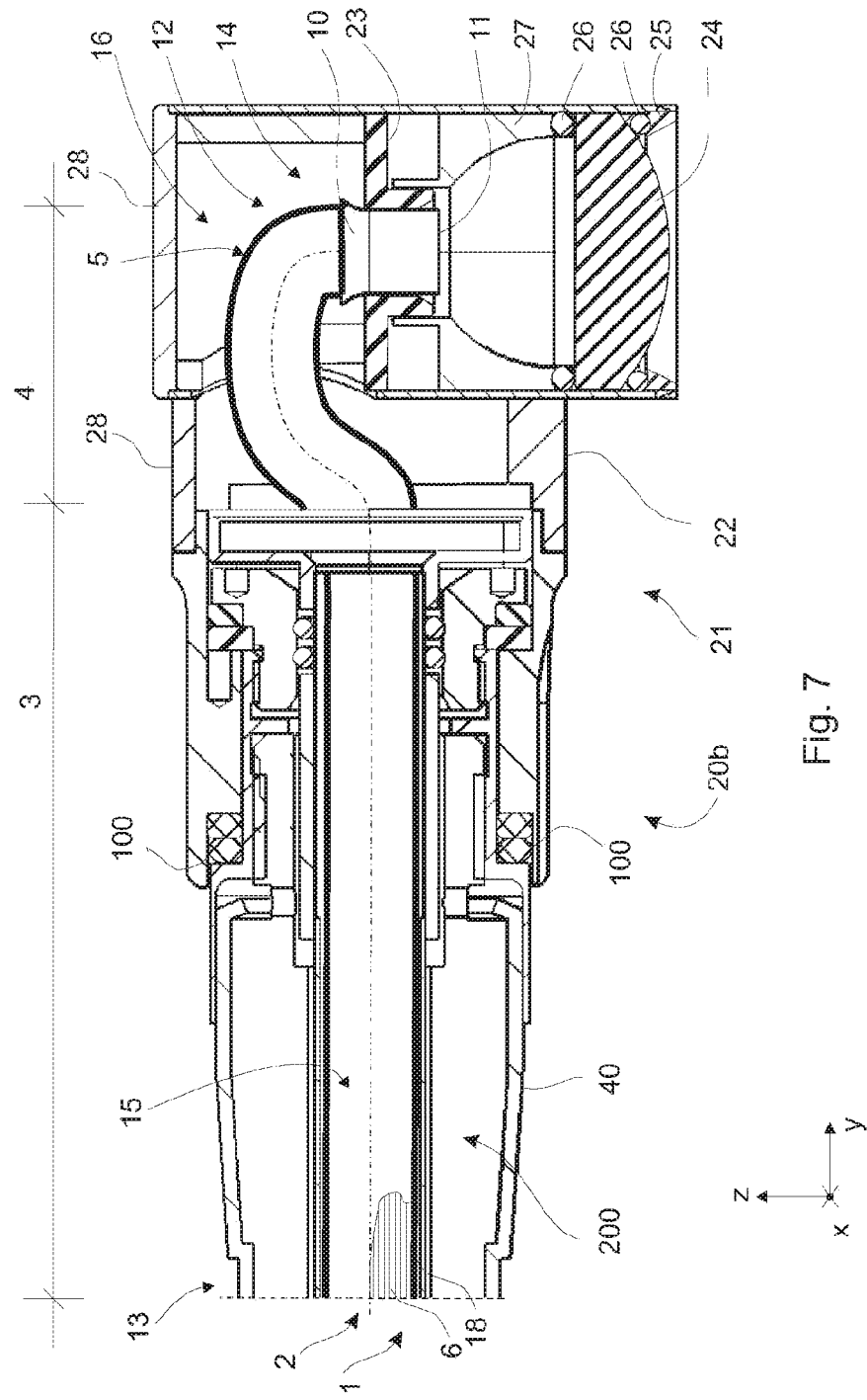
FIG. 7 shows a partial side view according to the section line G-G of the illumination shaft from FIG. 6, such that the illumination rod shown there in addition comprises a rotator head.

Preferably the bending paths of the subsidiary strands 16.1 and 16.2 in the respective planes of the X-Y-Z coordinates system are such that the second, curved portion 4 formed by the connecting portions 5 is suited for use in the illumination rod 20b shown in FIGS. 6 and 7. The curved portion 4 and the connecting portion 5, which maintains the bending, however, can also have other bending paths that are not shown in the drawings. Production of the curved second portion 4 by means of the connecting portion 5 is arranged in such a way that the curved second portion 4 and also the light-emitting end portion 14 can be adjusted to the required conditions or housing geometric shapes, depending on the particular application. The light conductor 1 shown in FIG. 3 can be used in the illumination rod 20 shown in FIGS. 6 and 7.

FIG. 4 shows a possible embodiment of the inventive light conductor 1 with a main strand 15 with a predetermined surface cross-section A, which extends in trident shape into three subsidiary strains 16.1 through 16.3, each with a predetermined surface cross-section B1 through B3. The three subsidiary strands 16.1 through 16.3 configure the curved portion 4, which is held in the curved shape in the particular connecting portion 5 by the hardened cementing agent. The individual subsidiary strands 16.1, 16.2 and 16.3 in the respective planes of the X-Y-Z coordinates system are provided with a corresponding curve and bend ratios $r_{xy}$, $r_{yz}$ and/or $r_{xz}$, so that the light-emitting end portions 14.1 through 14.3 can be inserted into the corresponding recesses of an illumination apparatus. If necessary, the respective subsidiary strands can also point in different directions, depending on how the recesses for the light-emitting end portions 14 are positioned in the illumination apparatus.

Figure 5:
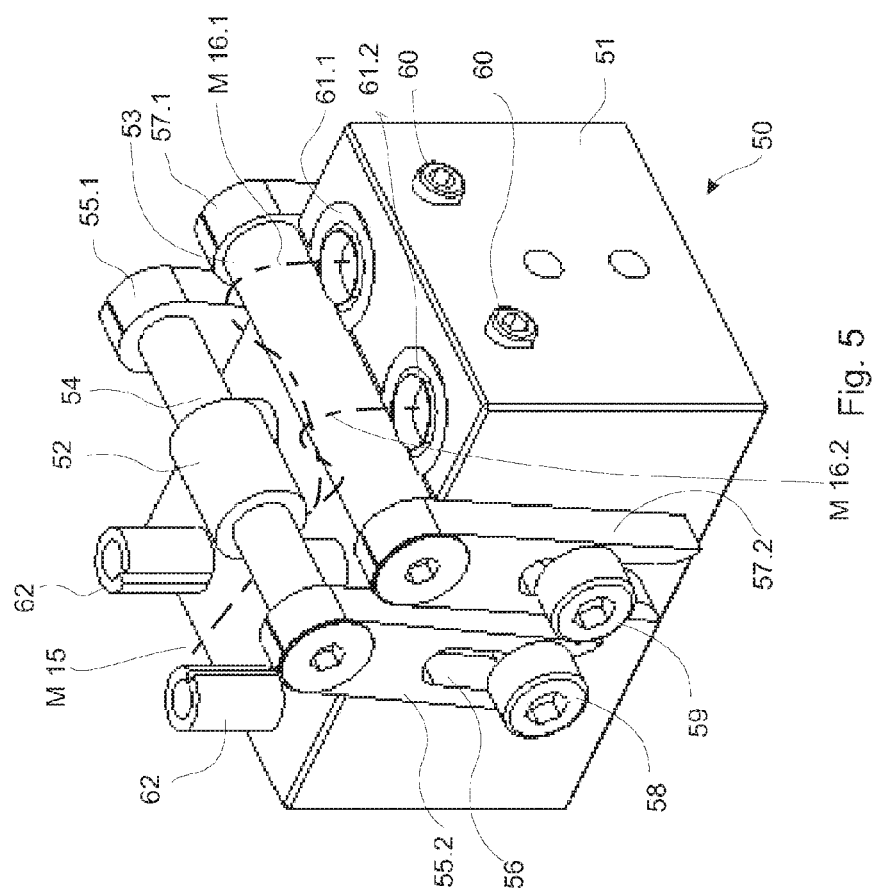
FIG. 5 shows a bending apparatus or curving the connecting portion of the light conductor shown in FIG. 3.

FIG. 5 shows a bending apparatus that is used in the method for producing the inventive light conductor 1, as shown in FIG. 3.

The bending apparatus 50 comprises a housing 51, which preferably is produced from a material that, without any significant reshaping, can withstand pressures and temperatures that arise in an oven while the cementing agent 8 hardens.

The bending apparatus for producing the inventive light conductor comprises a pressure or bending roller 52 and a deflecting roller 53. The pressure and bending roller 52 is fastened via a crossbeam 54 to the housing 51 by means of a first and a second pivot arms 55.1, 55.2 on the housing, such that the first and second pivot arms 55.1, 55.2 each comprise a recess 56, which allows an upward and pivoting sliding of the first and second pivot arms 55.1, 55.2. The required position of the first and second pivot arms 55.1, 55.2 and thus the position of the crossbeam 54 can be fixed by means of a locking screw 59, which engages in the recess 56 of the respective pivot arm 55.1, 55.2, here in the form of a socket screw.

The deflecting roller 53 comprises a crossbeam, essentially circular in cross-section, which has a predetermined diameter and likewise is mounted with a third and fourth pivot arms 57.1, 57.2 on the housing 51 so that it is movable in height and by pivoting. The desired position of the third and fourth pivot arms 57.1, 57.2 and thus the position of the deflecting roller 53 can likewise be fixed by means of a locking screw 59, which engages in the recess 56 of the respective pivot arm 57.1, 57.2 and here takes the form of a socket screw.

The cross-section of the deflecting roller 53 can be configured as rectangular, multi-angular or elliptical depending on the required curvature of the connecting portion 5 of the light conductor 1.

In proximity to the deflecting roller 53 on the upper part of the housing 51 of the bending apparatus 50, receiver cups 61.1 and 61.2 are provided for the light-emitting end portions 14.1 and 14.2. Said receiver cups 61.1 and 612 are replaceably mounted in the housing 51 in boreholes and can be fixed in place by means of setscrews 60.

To configure the required bend or curvature of the second curved portion 4 of the light conductor 1, instead of or in combination with the bending apparatus it is also possible to use a shaping bowl (not illustrated) in which a recess or cavity is formed and by which the fiber bundle is brought into the required bending by inserting the fiber bundle. The bowl is either dimensionally stable in itself, so that the fiber bundles can support themselves on the cavity wall of the casing and assume its given bend, or else it can be configured flexibly in such a way that the bowl can be used in combination with the bending apparatus, such that the bowl can both have forming properties and also be of such flexible configuration that the bowl can be bent by the bending apparatus into the required shape or bend. The bowl is preferably made of a material that can establish no firm contact with the cementing agent. The bowl is preferably of Teflon, as is the receiver cup 61.1, 61.2.

In addition, on the upper part of the housing 51 of the bending apparatus 50, in the vicinity of the crossbeam 54 of the pressure or bending roller 52, guide pins 62 are provided, which hold the main strand 15 of the inventive light conductor in place during the bending operation. The position of the light conductor 1 in the bending apparatus 50 is indicated by means of the center axes M15, M16.1 and M16.2 of the respective strand.

The inventive light conductor 1, as shown in FIG. 3, is produced as explained hereinafter, while the steps in the method are shown schematically in FIGS. 8A through 8F.

First a bundle 2 of optic fibers 6 is combined to form the main strand 15, preferably by binding with a cord, in such a way that a fiber bundle 2 is formed with a predetermined surface cross-section A of approximately 20 mm$^2$.

At the proximal end portion 12 of the main strand 15 hereby produced, a suitably sized shrink hose 18 can be pulled on, as shown in FIG. 8A.

In the next step, to configure the Y-shaped branching subsidiary strands 16.1 and 16.2 from the main strand 15, two fiber bundles are configured, with approximately equal-sized surface cross-section B2, that is, approximately 10 mm$^2$, in that the optic fibers 6, still loosely bound together, are accordingly divided up. A shrink hose 9 is then pushed onto each of the light-emitting end portions 14.1, 14.2 of the subsidiary strands 16.1 and 16.2. Afterward, a sleeve 10 is placed on each of the end portions 14.1, 14.2, such that a bundle portion of predetermined length extends out of the sleeve, as is shown in FIGS. 8B and 8C.

Before the shrink house 9 of the subsidiary strands 16.1 and 16.2 is pushed completely over the area that is intended to be configured as the connecting portion 5, a cementing agent 8 (see FIG. 8D) in a paste-like condition is applied over a predetermined length, preferably about 25 mm, into the respective bundle of optic fibers 6 of the subsidiary strands 16.1 and 16.2, so that every possible fiber 6 of the bundle is coated with cementing agent 8. The length of the connecting portion 5 that is to be provided with cement can also be shorter or longer depending on the required curvature. The coating or application of the paste-like or fluid cementing agent 8 preferably occurs in such a way that the portion 5 that is to be coated with the cementing agent 8 is unfolded in fan-like manner as indicated in FIG. 8D, and the cementing agent is applied to and massaged into the unfolded fiber bundle 2 by means of an applicator tool, such that all possible optic fibers 6 should be coated with the cementing agent 8.

The cement or cementing agent 8 is preferably massaged in by means of an applicator tool in such a way that each individual fiber 6 if possible is provided with the paste-like cementing agent. In the applicator tool used, care must be taken that the paste-like cementing agent can be easily applied to the bundle 2 of optic fibers. In this process, small wood sticks or brushes have stood out as appropriate tools for massaging-in the cementing agent.

Figure 8F:
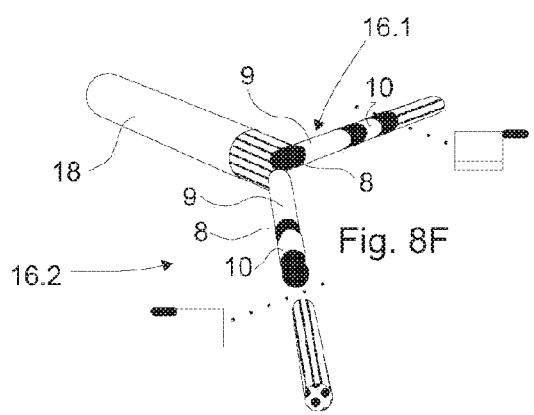
Figure 8G:
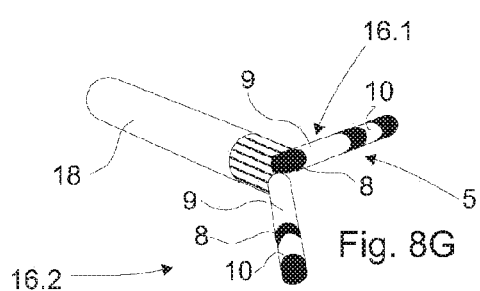
Figure 8H:
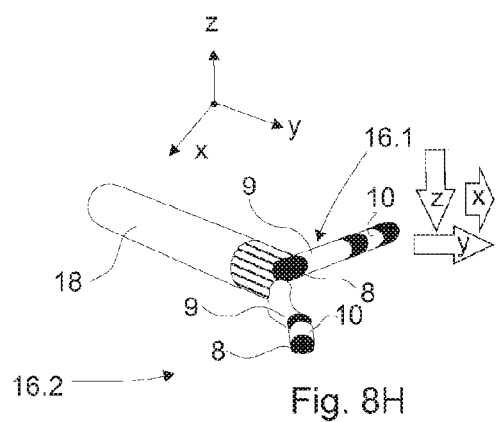
Figure 8I:
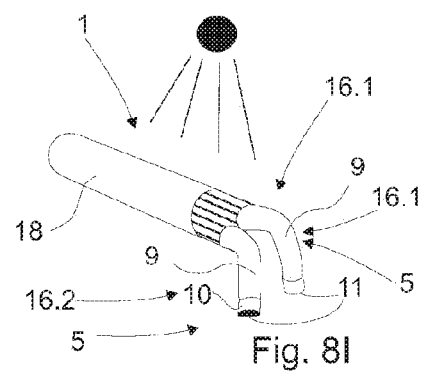

After the massaging application, the shrink hoses of the subsidiary strands 16.1, 16.2 are pulled over the areas of the fiber bundle into which the cementing agent has been applied, as indicated in FIG. 8E, such that the sleeves are accordingly pulled along. Fibers 6 provided with the cementing agent 8 now configure a connecting portion 5. Then, any possible excess length of optic fibers 6 not provided with cementing agent is severed from the light-emitting end portion 14 on the frame or sleeve 10 with a suitable cutting apparatus, as indicated in FIG. 8F with the cleaver symbol, so that a plug-like connection is configured, which can be inserted into recesses 61 of the bending apparatus 50 (see FIG. 5) or a recess 23 of an illumination rod (see FIGS. 6 and 7) and in order to produce the connecting area 5, as in FIG. 8G, formed in the subsidiary strands 16.1 and 16.2. Then the connecting portion 5 provided with the still paste-like cementing agent 5 is bent into the required bent form as indicated schematically in FIG. 8H with the help of a bending apparatus 50 or a corresponding bowl. To harden the cement so that the cement maintains the required curvature, the light conductor 1 together with the bending apparatus is hardened by raised temperature, as indicated in FIG. 8I. This can be performed in a suitable oven.

Shown in FIG. 5 is the bending apparatus 50, with which the connecting portion provided with paste-like cementing agent 8 can be brought into the required curvature and kept in it until the cementing agent has hardened and acts as a support frame and curvature of the optic fibers 6 can be maintained.

If the bending apparatus shown in FIG. 5 is used, to produce the curvature of the fibers 6 each of the light-emitting end portions 14 provided with the sleeve 10 are inserted into the respective receiver cup 61 of the bending apparatus 50. For better clarity, only the center axes M15, M16.1 and M16.2 of the light conductor 1 are shown. The connecting portion 5 provided with non-hardened cementing agent 8 is placed on the diverging roller 53, and the flexible portion 3 bordering on the connecting portion 5 is fixed in place below the pressure and bending roller 52. The pressure and bending roller 52 then presses the subsidiary strands 16.1 and 16.2 into the required bend against the diverging roller 53 or downward in the direction toward the housing 51, such that the main strand 15 of the bundle 2 is held in place by guide pins 62. It is essential in curving the subsidiary strands 16.1 and 16.2 that the cementing agent is still in non-hardened condition and that displacing the individual optic fibers 6 with respect to one another in curving allows the desired shape, so that no forced tensions develop in the optic fibers 6.

After the optic fibers 6 together with the paste-like, non-hardened cementing agent 8 are brought to the desired bend, the cementing agent 8 is then hardened by temperature increases in an oven. After the cement or cementing agent 8 has hardened, the optic fibers 6 are held in the connecting portion B5 by the hardened cementing agent free of tension, such that in the hardening process the shrink hoses on the main and subsidiary strands firmly surround the respective fiber bundles.

Usually the cements used as cementing agent, in non-hardened condition and before application to the fiber bundle, have thixotropic properties, that is, the viscosity or fluidity of the cement can be adjusted to the desired paste-like viscosity by mechanical impacts such as jiggling or shaking of a cement that is, for example, too viscous. The cementing agent preferably has, upon application, a viscosity that is comparable to that of toothpaste at room temperature. Two-component cements are preferably used that before insertion in the fiber bundle 2 are mixed in such a way that a homogeneous blend of the two components is achieved.

Shown in FIG. 6 is an illumination apparatus, in particular an illumination shaft 20a, in which the embodiment of the inventive light conductor 1 shown in FIG. 3 can be used with a Y-shaped branching connecting portion 5. The illustrated illumination apparatus is an illumination shaft 20a, which is suited for use in medical procedures. The illumination shaft 20a is produced from materials that can withstand repeated medical sterilization, in particular in an autoclave.

FIG. 6 shows a perspective depiction of the illumination shaft 20a with a dimensionally stable housing 22 and a flexible cable 40. The housing 22 is configured to receive the light-emitting end portions 14.1 and 14.2 of the inventive light conductor 1 according to FIG. 3, in particular the sleeve 10 applied thereto, and of an optical lens 24 (see FIG. 7). For improved clarity, the upper covering 28 of the illumination shaft 20a is depicted in a raised, disassembled position with respect to the housing 22 and all that is seen of the inventive light conductor according to FIG. 3 are the sleeves 10 and the course of the center axes M15, M16.1, M16.2 of the main strand 15 and of the connecting strands 16.1 and 16.2. The flexible second portion 4 of the bundle 2 of optic fibers 6, preferably the main strand 15, is housed in the flexible cable 40 in such a way that the bundle 2 is held flexibly by the cable. Receivers 23.1 and 23.2 are provided to accept the sleeve 10 or the light-emitting end portions 14.

The main strand 15 or the flexible portion 3 of the inventive light conductor 1 is positioned in the cable 40. The first and second subsidiary strands 16.1 and 16.2 are housed in the dimensionally stable housing 22 of the illumination rod 20b.

In the embodiment of the inventive light conductor 1 shown in FIG. 3, the respective subsidiary strands 16.1 and 16.2 are each provided at their light-emitting end portion 14.1, 14.2 with a sleeve 10.1, 10.2, which can be inserted in a corresponding receiver 23.1, 23.2 of the housing 22 of the illumination rod 20b of the rotary head 21 shown in FIG. 6 and can be blocked there with corresponding measures. For example, the sleeves 10 of the light conductor 1 can be fixed at the receivers 23.1, 23.2 of the housing 22 of the illumination rod 20b by a corresponding cementing agent.

FIG. 7 shows in a partial sectional view another embodiment of the inventive light conductor 1, as shown in FIG. 1, together with an illumination rod 20b, which is distinguished from the rotary shaft shown in FIG. 6 in that the illumination rod comprises a rotary head such that the section line G-G in FIG. 6 is used for the illumination shaft 20a for greater clarity. The illumination shaft 20a illustrated in FIG. 6 is distinguished in addition from the illumination rod 20b shown in FIG. 7 in that the rotary head 21 is configured to receive the single-strand light conductor 1 shown in FIG. 1.

The illumination rod 20b of FIG. 7 comprises the rotary head 21, which is mounted to rotate with respect to a cable 40 about the center axis M. The rotary head 21 comprises a housing 22. The housing 22 comprises a receiver 23 for the sleeve 10 of the light-emitting end portion 14 of the light conductor 1. Also mounted in the housing 22 is an optical lens 24. Said optical lens 24 can, for example, be a convergent lens or a diffuser lens or any other appropriate optical apparatus. In the frame 26 in FIG. 7 a plane-convex convergent lens 24 is shown, such that the plane surface of the convergent lens 24 is facing toward the light-emitting end portion 14 of the light conductor 1. The optical lens is positioned between insulating rings 26. Between the receiver 23 and the optical lens 24, a spacer 27 is provided. Said spacer 27 is required in order to be able to position the optical lens 24 at an appropriate distance from the end surface 11 of the light conductor 1.

The inventive light conductor 1 is inserted with the sleeve 10 at the light-emitting end portion 14, which is configured by the first curved end portion 12, in a receiver 23 of the housing 22 of the illumination rod 20. The receiver 23 is preferably configured so that the sleeve 14 of the light conductor 1 is retained in the receiver 23 by interference fitting. It is also possible to fix the sleeve 10 in the receiver 23 by means of a cement. It is further possible to fix the sleeve 10 in place by means of a releasable connecting agent such as a locking screw (not illustrated), which is provided in the area of the receiver 23.

As can be seen from FIG. 7, in the housing of the illumination rod 20 no additional holding or support apparatuses are required for the light conductor 1 in the area of the connecting portion 5 that would make production of the housing 22 more complex and more expensive. The dimensionally stable connecting portion 5 of the light conductor 1 inserted in the housing 22 facilitates not only the process of budding into the housing but also offers protection against breaking and buckling for the optic fibers 6 embedded in the curved portion 4 and in the connecting portion 5.

The optic fibers 6 of the bundle 2 of the light conductor 1 used in the illumination rod 20b consist of glass fibers, in particular glass fibers with a glass core 600 with a diameter of approximately 70 micrometers, which is enclosed by a glass coating 601 with a thickness of about 2.5 micrometers (see FIG. 1E). The illuminating rod 20b with the rotary head 21 is configured in the preferred embodiment for use of the single-strand light conductor 1 shown in FIG. 1 and comprises only one receiver 23. The rotary head 21, however, can also be provided with two receivers 23.1, 23.2, so that the two-strand light conductor 1 shown in FIG. 3 can be used.

The cable 40 is connected with the rotary head 21 of the housing 22 in fluid-tight manner via insulations 100, so that the torsion movement of the rotary head 21 is possible about the center axis M.

The flexible first portion 3 of the inventive light conductor 1 is enclosed in the cable 40 in such a way that the individual optic fibers 6 have the possibility, at least in the first portion in XY and Z directions, to shift with respect to one another, in particular when the cable 40 is reshaped to direct the rotary head 21.

The cable 40 is preferably made of a flexible, that is, pliable protective material, which is customary in medical apparatuses with a flexible supply hose such as endoscopes. The inventive light conductor 1 is retained in place inside the housing by means of the receiver 23. The bundle 2 of the inventive light conductor 1 in the first flexible portion 3 is preferably provided with a cladding 18. Said cladding 18 is a protective hose 18 of a material that is especially low in friction.

In the cavity 200 between the cladding 18 and the mantle of the cable 40, a spiral coil is preferably provided, which restricts the room to maneuver for the bundle of optic fibers 6, to alleviate the breaking of individual optic fibers 6 in actuating and operating the illumination rod.

The end portion 13, positioned proximally to a light source (not illustrated), comprises a coupling apparatus (not shown). The individual optic fibers are connected with the light-emitting light source b, the coupling apparatus of the illumination rod 20 in such a way that the light emitted by the light source is transmitted from the proximal end portion 13 of the light conductor all the way to the distal second end portion 3 positioned to the light source and can exit from the light-emitting end portion 14. The light source preferably emits cold light. A xenon light source is preferably used as the light source. It is also conceivable, however, that the light source could be a halogen light source or an LED light source.

The inventive light conductor is not restricted to being used in the aforementioned illumination rod. Rather, the inventive light conductor can be used in other illumination apparatuses, in particular medical ones, such as endoscopes, exoscopes or headlamps.

The invention claimed is:
1. A light conductor comprising:
a first portion having a first end portion;
a curved second portion configured as a connecting portion having a second end portion; and
a bundle of optic fibers for transmitting light of a light source coupled from the first end portion to the second end portion, wherein the optic fibers in the second portion are fixed with respect to one another, essentially free of tension, by means of a hardened cementing agent while maintaining a curvature in the second portion, wherein the cementing agent at least party surrounds outer peripheral surfaces of the optic fibers and combines the optic fibers with one another so that the cementing agent forms a support frame into which individual or several or all optic fibers are embedded in order to constitute the connection portion.

2. The light conductor of claim 1, wherein on the second portion a flexible hose is mounted to stabilize the second portion.

3. The light conductor of claim 1, wherein on the first or second end portion of the light conductor a frame is mounted for insertion into a receiver recess for mechanical fastening of the light conductor.

4. The light conductor of claim 3, wherein the frame is of sleeve-shaped configuration and the ends of the optic fibers at the outlet end of the frame form altogether a convex and/or concave and/or level surface, which is preferably polished or smoothed.

5. The light conductor of claim 4, wherein the frame is a sleeve made of metal, synthetic material or a combination of metal and synthetic material.

6. The light conductor of claim 2, wherein the flexible hose of the connecting portion is contiguous with the frame.

7. The light conductor of claim 1, wherein the first and second portions are configured in such a way that the optic fibers in the first portion comprise a first surface cross-section and in the second portion form a first and second subsidiary bundle into which the optic fibers of the first portion branch in a Y shape and in each case comprise a surface cross-section that is smaller than the first surface cross-section.

8. The light conductor of claim 1, wherein the optic fibers are glass fibers and/or synthetic fibers.

9. The light conductor of claim 8, wherein the glass fibers comprise a class core with a diameter of approximately 20 to 500 micrometers, which is surrounded with a glass coating or synthetic coating.

10. The light conductor of claim 1, wherein the curvature of the connecting portion has a bend radius ($r_{xy}$, $r_{xz}$, $r_{yz}$) with constant or varying curvature.

11. The light conductor of claim 1, wherein, to form the connecting portion, the cementing agent forms a support frame into which individual or several or all optic fibers are embedded so that no additional support apparatuses, especially in a housing, are required for the connecting portion.

12. An illumination apparatus having a light conductor of claim 1, wherein the light conductor is provided in a medical apparatus, in particular in a headlamp, an endoscope, an exoscope, an illumination shaft or an illumination rod with or without a pivot lens.

13. A method for bending a light conductor that is made up of optic fibers and having a first portion and a second portion that is configured curved as a connecting portion, said method comprising the following steps:

coating the optic fibers of the second portion of the light conductor, which is to be produced as a connecting portion, with a cementing agent in a paste-like condition;

next, curving the second portion into a predetermined bent shape, while the cementing agent is still in a paste-like condition; and hardening the cementing agent while maintaining the curvature of the second portion until the second portion forms the dimensionally stable connecting portion with predetermined bent shape.

14. The method of claim 13, wherein prior to applying the cementing agent, a flexible hose, in particular a shrink hose, is pulled over a portion of the optic fibers situated close to the second portion and after coating the optic fibers with the cementing agent the flexible hose, in particular the shrink hose, is pulled over the second portion, which is coated with cement.

15. A light conductor having a bundle of optic fibers and a curved portion, wherein the optic fibers are fixed in place with respect to one another, at least partly free of tension, by means of a hardened cementing agent, the light conductor produced according to the method of claim 13.

* * * * *